US006804548B2

(12) United States Patent
Takahashi et al.

(10) Patent No.: US 6,804,548 B2
(45) Date of Patent: Oct. 12, 2004

(54) IRRADIATION SYSTEM AND ITS IRRADIATION TARGET MOVEMENT MONITORING METHOD, AND IRRADIATION TARGET POSITION RECOGNIZING METHOD

(75) Inventors: Shuichi Takahashi, Tokyo (JP); Katsunobu Muroi, Tokyo (JP); Yoshikazu Nakajima, Osaka (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 41 days.

(21) Appl. No.: 09/964,481

(22) Filed: Sep. 28, 2001

(65) Prior Publication Data

US 2002/0077545 A1 Jun. 20, 2002

(30) Foreign Application Priority Data

Dec. 14, 2000 (JP) .................................... 2000-380869

(51) Int. Cl.[7] .............................................. A61B 5/00
(52) U.S. Cl. .................................... 600/427; 378/65
(58) Field of Search ............................ 600/427, 429; 378/65

(56) References Cited

U.S. PATENT DOCUMENTS

| | | | |
|---|---|---|---|
| 5,588,430 A | | 12/1996 | Bova et al. |
| 6,052,611 A | * | 4/2000 | Yanof et al. ................. 600/429 |
| 6,144,875 A | * | 11/2000 | Schweikard et al. ........ 600/427 |
| 6,219,403 B1 | * | 4/2001 | Nishihara ..................... 378/65 |
| 6,307,914 B1 | * | 10/2001 | Kunieda et al. .............. 378/65 |

FOREIGN PATENT DOCUMENTS

| | | | |
|---|---|---|---|
| JP | 01242074 A | * 9/1989 | ............ A61N/5/10 |
| JP | 11501534 | 2/1999 | |

OTHER PUBLICATIONS

Sato, Yoshinobu et al.: "Tissue Classification Based on 3D Local Intensity Structure for Volume Rendering" IEEE Transactions on Visualization and Computer Graphics, vol. 6, No. 2, pp. 160–180 Apr.–Jun. 2000 "Linac Scappel" Radiocameras System Kobayashi Sofamor Danek.

F. Maes et al.: "Comparative evalution of multiresolution optimization strategies for multimodality image registration by maximization of mutual information" Oxford University Press, Medical Image Analysis vol. 3, No. 4, pp. 373–386, 199.

* cited by examiner

Primary Examiner—Ruth S. Smith
(74) Attorney, Agent, or Firm—Birch, Stewart, Kolasch & Birch, LLP

(57) ABSTRACT

A radiation system includes a measuring section of position and direction for computing relative position and direction between various components of the system; an irradiation condition correcting section for obtaining positions and directions of the irradiation target regions in the images using computation results obtained by the measuring section of position and direction and compared results obtained by comparing the irradiation target regions in the images taken by an irradiation target image acquisition section, and for correcting the irradiation conditions such that the obtained position and direction are reflected in the irradiation conditions; and a control section for controlling the radiation to the irradiation target region in response to the irradiation conditions obtained as a result of the correction by the irradiation condition correcting section. The irradiation system can solve a problem of a conventional system in that although the conventional system is effective for the radiation therapy to a head region, its irradiation accuracy is degraded in a trunk region such as abdominal organs where the effect of the body movement such as respiration is greater than in the head region, and hence the position and direction of the irradiation target is continuously changing.

11 Claims, 4 Drawing Sheets

IRRADIATION SYSTEM AND ITS IRRADIATION TARGET MOVEMENT MONITORING METHOD, AND IRRADIATION TARGET POSITION RECOGNIZING METHOD

BACKGROUND OF THE INVENTION

1. Field of the Invention

The present invention relates in general to an irradiation system used for radiation therapy administering radiation to an irradiation target such as a tumor, and more particularly to an irradiation system and its irradiation target movement monitoring method, and an irradiation target position recognizing method that can administer radiation by precisely recognizing position and direction of an irradiation target without using a positioning frame, while directly monitoring the position and direction of the target being irradiated.

2. Description of Related Art

The radiation therapy is a treatment to reduce or eliminate tumors by intensively administering radiation to the tumors of a patient. To achieve such a radiation therapy, it is necessary to administer radiation to a tumor, a target to be irradiated, intensively and in proper amount. At the same time, it is necessary to decrease radiation exposure to surrounding healthy tissue as much as possible.

Thus, the radiation therapy is carried out such that excessive irradiation to the tumor and its surrounding healthy tissue is suppressed by administering radiation from multiple directions with particular emphasis on the tumor as the irradiation target, so that only the tumor is intensively irradiated.

To achieve effective radiation only to the target intensively and precisely, it is essential to measure the position and direction of the target, and to decide the pros and cons of the irradiation by computing the relative position and direction between the target and a irradiation head from the computed results.

More specifically, a set of image data of an irradiation region including the target tumor is captured before irradiation, and the relative position and direction between the target and the irradiation head is measured from the set of image data, thereby planning the radiation therapy treatment in terms of the directions and irradiation dose along with the duration and the number of times of the irradiation to implement the radiation therapy according to the plan.

In such a radiation therapy as described above, there is a method to bury a marker near the target tumor, as one of the techniques to measure the position and direction of the target accurately. In this method, fixing the relative position and direction between the marker and irradiation head will enable the position and direction between the target and irradiation head to be measured with respect to the marker regardless of the variations in the position and direction of the target due to movement of the patient, and hence allows the radiation with fixing the relative position and direction between the target and irradiation head.

This method, however, is greatly invasive to the patient in that the marker is buried into the body. Thus, it is preferable to avoid this method as much as possible considering the stress imposed on the patient.

In view of this, another radiotherapy is proposed that can accurately measure the position and direction of the target non-invasively without setting the marker in the body of the patient. This method fixes a solid frame made of metal or the like on the surface of the head of the patient to precisely measure the position and direction between the target and irradiation head with respect to the frame, and administers radiation with fixing the relative position and direction between the target and the irradiation head.

This method utilizes the fact that there is little movement due to respiration or the like within the head because the brain is placed in the skull. Fixing the frame on the surface of the head and maintaining the fixed position can almost fix the relative position and direction between the frame and the target throughout the radiation. Furthermore, the relative position and direction between the frame and the irradiation device (irradiation head) can be accurately measured by fixing the frame on a treatment table or by installing a position and direction sensor on the frame.

Thus, the precise measurement of the position and direction of the frame enables precise position recognition and irradiation of the target tumor.

However, since the frame is usually fixed on the patient from the time of image measurement of the irradiation region including the target tumor for planning the radiation therapy to the time of administering the actual irradiation, the stress imposed on the patient is considerable. In addition, since the frame is fixed rather strong to prevent the frame from shifting, it is unavoidable that the patient has feelings of restraint and pressure. Thus, position recognition of the target tumor without using the frame, if implemented, will serve to improve the therapeutic environment of the patient.

As techniques of implementing the non-invasive radiation therapy of a head region, there are "Repeat fixation for frameless stereotactic procedure" disclosed in U.S. Pat. No. 5,588,430, and a radiocamera system of Kobayashi Sofamor Danek utilizing this patent.

FIG. 5 schematically shows a configuration for recognizing the position of an irradiation target in the conventional irradiation system, the "Repeat fixation for frameless stereotactic procedure" disclosed in the foregoing U.S. Pat. No. 5,588,430. In this figure, the reference numeral 51 designates a patient's head including an irradiation target tumor; 52 designates a treatment table on which the patient lies down; and 53 designates a head ring with a structure simpler than the conventional frame, for securing the patient's head 51 to the treatment table 52. The reference numeral 54 designates a bite plate having LEDs (Light Emitting Diodes) mounted thereon for measuring the position of the body surface of the patient; and 55 designates a mouthpiece that has the bite plate 54 attached thereto, and is bitten by the patient.

Next, the operation of the conventional method will be described.

First, the patient's head 51 is secured to the treatment table 52 by the head ring 53. Then, the bite plate 54 serving as a marker for measuring the position and direction is attached to the mouthpiece 55 the patient bites. The bite plate 54 is almost immobilized with respect to the patient's head 51 during the radiation. Accordingly, the relative position and direction between the bite plate 54 and the irradiation target in the head 51 is assumed to be almost invariable. Therefore, measuring the three-dimensional position and direction of the bite plate 54 makes it possible to estimate the position and direction of the target tumor indirectly.

In addition, since the irradiation system allows the patient to be precisely repositioned by only biting the bite plate 54, it is unnecessary for the patient to wear the head ring 53 in the second and the following radiation, thereby reducing the stress on the patient during the therapy.

With the foregoing configuration, the conventional irradiation system is effective for the radiation therapy to a head region. However, it presents a problem in that the irradiation accuracy is degraded in trunk regions such as abdominal organs that are more affected by the body movement like respiration than the head region is, and that are continuously fluctuating the position and direction of the irradiation target.

This problem will be described in more detail.

In the radiation therapy applied to a tumor emerging in a trunk region such as an abdominal organ, since the effect of the body movement like respiration is greater than in the head region, the position and direction of the target tumor continues to vary during the irradiation. Thus, the variations in the position and direction of the irradiation target due to changes in the patient's posture become greater than those expected in the planning of the radiation therapy. In addition, being different from the head region, the trunk region usually has no bones usable for fixing a frame near the target tumor, which makes it difficult for the frame to be secured on the body surface.

As a result, it is difficult to immobilize the relative position and direction between the target to be irradiated and a jig such as a frame for measuring the position of the body surface.

Besides, to plan a radiation treatment, it is more common to use a set of image data of the irradiation region including the irradiation target acquired before the planning than to use a set of image data taken just before the irradiation.

Thus, during the planning of the radiation therapy, the posture of the patient can vary, and hence the position and direction of the irradiation target. As a result, the irradiation accuracy has some error between the planning of the radiation therapy and the actual irradiation.

Considering the risk rate of bringing about the error of the irradiation accuracy, the actual irradiation is performed assuming some margin around the region including the target tumor. This presents another problem of causing undue radiation exposure to the healthy tissue surrounding the target tumor.

As described above, taking account of the greater error in the irradiation accuracy of the trunk region than that of the head region, the irradiation margin of the trunk region must be set greater than that of the head region. Therefore, the radiation exposure to the healthy tissue surrounding the irradiation target is greater in the trunk region than in the head region.

The conventional irradiation system disclosed in the foregoing U.S. Pat. No. 5,588,430 employs the mouthpiece 55 to which the bite plate 54 is attached, so that it is not necessary to fix a frame to the patient's head 51 during the period from the image acquisition of the set of image data of the irradiation region including the target to the actual irradiation. However, since the head ring 53, a kind of frame, is fixed on the patient's head 51, and the mouthpiece 55 is inserted into the mouth, it is unavoidable that the patient has some feelings of restraint and pressure.

SUMMARY OF THE INVENTION

The present invention is implemented to solve the foregoing problem. It is therefore an object of the present invention to provide an irradiation system and its irradiation target movement monitoring method, and an irradiation target position recognizing method capable of reducing the stress imposed on the patient, and performing precise radiation therapy not only to the head region, but also to the trunk region without using any positioning frame of the irradiation target.

According to a first aspect of the present invention, there is provided a radiation system comprising: irradiation target positioning means for placing an object having an irradiation target to be subjected to irradiation; irradiation target imaging means for taking images of an irradiation target region including the irradiation target; irradiation means for administering radiation to the irradiation target region according to prescribed irradiation conditions; position and direction measuring means for measuring positions and directions of the irradiation target positioning means, the irradiation target imaging means and the irradiation means, and for computing relative positions and directions between them; irradiation condition correcting means for obtaining position and direction of the irradiation target region in the images using computation results of the position and direction measuring means and compared results obtained by comparing the irradiation target regions in the images successively taken by the irradiation target imaging means, and for correcting the irradiation conditions in which the obtained position and direction is reflected; and control means for controlling the radiation to the irradiation target region in response to the irradiation conditions obtained as a result of the correction by the irradiation condition correcting means.

Here, the position and direction measuring means may measure positions and directions of the irradiation target positioning means, the irradiation target imaging means, and the irradiation means in a 3D coordinate system.

The irradiation target imaging means may comprise a plurality of imaging devices of different modality, and the irradiation condition correcting means may obtain the position and direction of the irradiation target region in the images using computation results obtained by the position and direction measuring means and compared results obtained by comparing the irradiation target region in the images taken by the imaging device of the same modality among the images successively taken by the plurality of imaging devices of different modality.

The irradiation target imaging means may comprise: a high resolution imaging device for taking high resolution 3D images of the irradiation target region which are used for setting the irradiation condition; and a real-time imaging device for taking high resolution 3D images of the irradiation target region before and during irradiation, wherein the irradiation condition correcting means may obtain the position and direction of the irradiation target regions in the images using the computation results obtained by the position and direction measuring means, compared results obtained by comparing the irradiation target regions in the images taken by the high resolution imaging device, and compared results obtained by comparing the irradiation target regions in the images taken by the real-time imaging device, and may correct the irradiation conditions using the images which are acquired by the high resolution imaging device and by the real-time imaging device, and in which the obtained positions and directions are reflected.

According to a second aspect of the present invention, there is provided an irradiation target movement monitoring method of an irradiation system including irradiation target positioning means for placing an object having an irradiation target to be subjected to irradiation, irradiation target imaging means for taking images of an irradiation target region including the irradiation target, and irradiation means for administering radiation to the irradiation target region according to prescribed irradiation conditions, the irradiation target movement monitoring method comprising: an image acquisition step of successively taking images of the irradiation target region by the irradiation target imaging means; a position and direction measuring step of measuring positions and directions of the irradiation target positioning means, the irradiation target imaging means and the irradiation means, and of computing relative positions and directions between them; and an irradiation target monitoring step of obtaining positions and directions of the irradiation target regions in the images using computation results obtained by the position and direction measuring means and compared results obtained by comparing the irradiation target regions in the images successively taken in the image acquisition step.

Here, the irradiation target monitoring step may obtain the positions and directions of the irradiation target regions in the images using computation results obtained in the position and direction measuring step and compared results obtained by comparing the irradiation target regions in the images successively taken by the irradiation target imaging means of the same modality.

According to a third aspect of the present invention, there is provided an irradiation target position recognizing method of an irradiation system including irradiation target positioning means for placing an object having an irradiation target to be subjected to irradiation, irradiation target imaging means for taking images of an irradiation target region including the irradiation target, and irradiation means for administering radiation to the irradiation target region according to prescribed irradiation conditions, the irradiation target movement monitoring method comprising: an image acquisition step of successively taking images of the irradiation target region by the irradiation target imaging means; a position and direction measuring step of measuring positions and directions of the irradiation target positioning means, the irradiation target imaging means and the irradiation means, and of computing relative positions and directions between them; and a target position recognizing step of obtaining positions and directions of the irradiation target regions in the images using computation results obtained by the position and direction measuring means and compared results obtained by comparing the irradiation target regions in the images successively taken in the image acquisition step, and of correcting the irradiation conditions by reflecting the positions and directions in the images.

The target position recognizing step may obtain the positions and directions of the irradiation target regions in the images using computation results obtained in the position and direction measuring step and compared results obtained by comparing the irradiation target regions in the images successively taken by the irradiation target imaging means of the same modality.

DETAILED DESCRIPTION OF THE PREFERRED EMBODIMENT

The invention will now be described with reference to the accompanying drawings.

Figure 1:
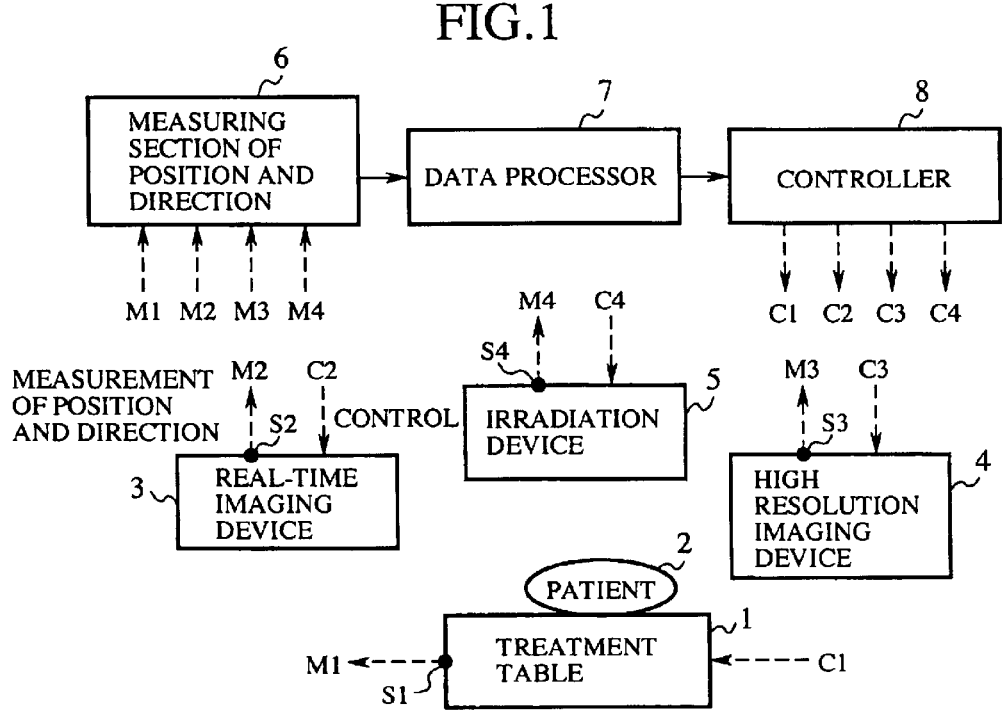
FIG. 1 is a block diagram showing a configuration of an embodiment of the irradiation system in accordance with the present invention.

FIG. 1 is a block diagram showing a configuration of an embodiment of the irradiation system in accordance with the present invention. In this figure, the reference numeral 1 designates a treatment table on which a patient 2 lies down, and to which a 3D position and direction sensor S1 is attached for detecting its position and directions to other components. The treatment table 1 includes a driving means not shown in this figure for changing its position and direction in response to control data C1 fed from a controller 8. The reference numeral 2 designates a subject for imaging having an irradiation target. In the example of FIG. 1, it is a patient having a tumor as an irradiation target. In the present invention, the subject for imaging having the irradiation target is not limited to a human being such as the patient.

The reference numeral 3 designates a real-time imaging device such as an echograph (irradiation target imaging means) for acquiring 3D images of an irradiation target region at a high resolution, which captures a set of image data consisting of images at respective imaging times. The real-time imaging device 3 corrects the imaging conditions of the irradiation target region in response to the control data C2 fed from the controller 8 such that it can acquire images at the highest resolution in the irradiation condition after varying the imaging condition of the images. The reference numeral 4 designates a high resolution imaging device (irradiation target imaging means) such as an X-ray CT (X-ray computerized tomography system) and an MRI (magnetic resonance imager) for taking the 3D images of the irradiation target region at a high resolution. The high resolution imaging device 4 does not take images of the irradiation target region successively in real time, but acquires a high resolution tomogram including the irradiation target region used for planning the radiation treatment (irradiation condition). The high resolution imaging device 4 corrects the imaging condition of the irradiation target region in response to the control data C3 fed from the controller 8 such that it can acquire the images at the highest resolution in the irradiation condition after varying the imaging condition.

The reference numeral 5 designates an irradiation device (irradiation means) for administering radiation to the irradiation target region in accordance with the irradiation plan. It radiates X-rays for medical usage, for example. Like the treatment table 1, the imaging probe of the real-time imaging device 3, the imaging head of the high resolution imaging device 4 and the irradiation head of the irradiation device 5 are provided with 3D position and direction sensors S2, S3 and S4, respectively. These sensors each detect their position and directions with respect to other components. The irradiation head of the irradiation device 5 has a driver for changing its position and direction in response to the control data C4 fed from the controller 8.

The reference numeral 6 designates a measuring section of position and direction (position and direction measuring means) for receiving detection signals M1–M4 indicating their positions and directions from the 3D position and direction sensors S1–S4, which are attached to the treatment table 1, the imaging probe of the real-time imaging device 3, the imaging head of the high resolution imaging device 4 and the irradiation head of the irradiation device 5, respectively, and for computing the relative positions and directions between them from the detection signals M1–M4. The reference numeral 7 designates a data processor (irradiation condition correcting means) for obtaining the position and direction of the irradiation target region in the work space for measurement in the images taken by the real-time imaging device 3 or by the high resolution imaging device 4 from the computation results by the measuring section of position and direction 6 and from the images taken by the real-time imaging device 3 and the high resolution imaging device 4, and for generating correction data by reflecting the positions and directions in the irradiation plan. The reference numeral 8 designates a controller (control means) for supplying the treatment table 1, real-time imaging device 3, high resolution imaging device 4 and irradiation device 5 with the control data C1–C4 for correcting the irradiation plan in accordance with the correction data fed from the data processor 7. Reference symbols S1–S4 designate the 3D position and direction sensors (position and direction measuring means) installed on the treatment table 1, the imaging probe of the real-time imaging device 3, the imaging head of the high resolution imaging device 4 and the irradiation head of the irradiation device 5. They can be a sensor using infrared rays, ultrasound or magnet.

The irradiation system of the present embodiment defines the positions and directions of its components in a 3D orthogonal coordinate system in the work space for measurement, which coordinate system includes the irradiation system and has its origin on the treatment table 1. It is assumed that all the following operations are carried out in the work space for measurement: the irradiation to the irradiation target region by the irradiation device 5; the capturing of the set of image data of the irradiation target region by the real-time imaging device 3 or by the high resolution imaging device 4; the superimposition and comparison of the image data of the set of image data; the extraction of the relationships between the set of image data and the radiation beam output from the irradiation device 5, and the operation of reflecting the relationships on each other; monitoring the movement of the irradiation target; and the recognition of the position and direction of the irradiation target.

Figure 2:
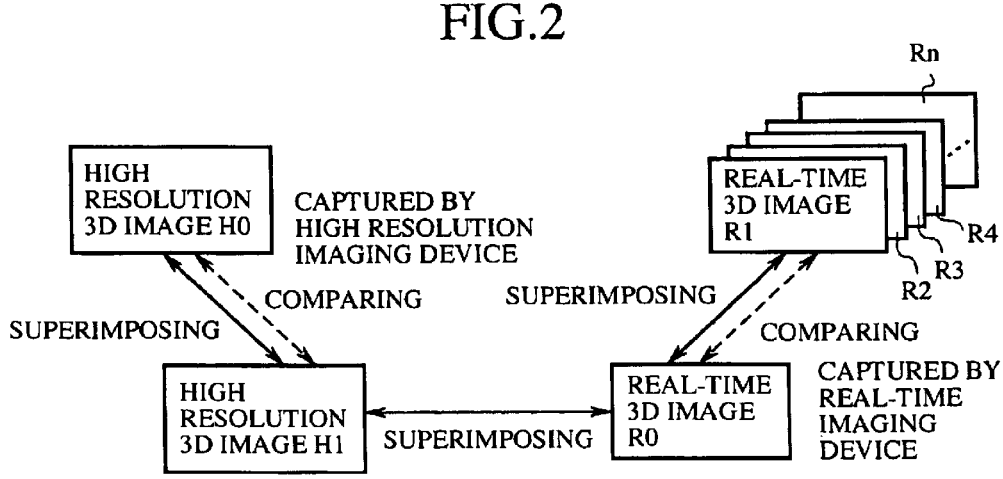
FIG. 2 is a diagram illustrating a processing of a set of image data captured by imaging devices of the irradiation system of the embodiment.

FIG. 2 is a diagram illustrating the processing of the set of image data captured by the imaging devices of the irradiation system of the present embodiment. In this figure, reference symbols H0 and H1 each designate an image including the irradiation target region taken by the high resolution imaging device 4; and R0–Rn each designate an image including the irradiation target region taken by the real-time imaging device 3. The present embodiment determines the position and direction of the irradiation target region by tracking and monitoring the movement of the irradiation target using the images including the irradiation target region taken by the imaging devices 3 and 4 rather than by tracking the movement of the patient 2 or his or her body surface as the conventional system. In addition, although the superimposition of the set of image data in the work space for measurement is carried out successively along the processing procedure, the comparison between the set of image data of the irradiation target region is carried out only between the images taken by the imaging device of the same modality.

More specifically, different modality imaging, which will bring about different physical parameters, will provide different boundaries for the same region extracted from the image data, thereby causing disagreement of the boundaries when comparing the regions of the image data between the sets of image data obtained by taking the same region in the different modalities. In view of this, the irradiation system of the present embodiment compares only the image data that are taken in the same modality. Accordingly, it is unnecessary to consider the sameness of the extracted boundaries of the region between the different modalities.

Next, the operation of the present embodiment will be described.

Figure 3:
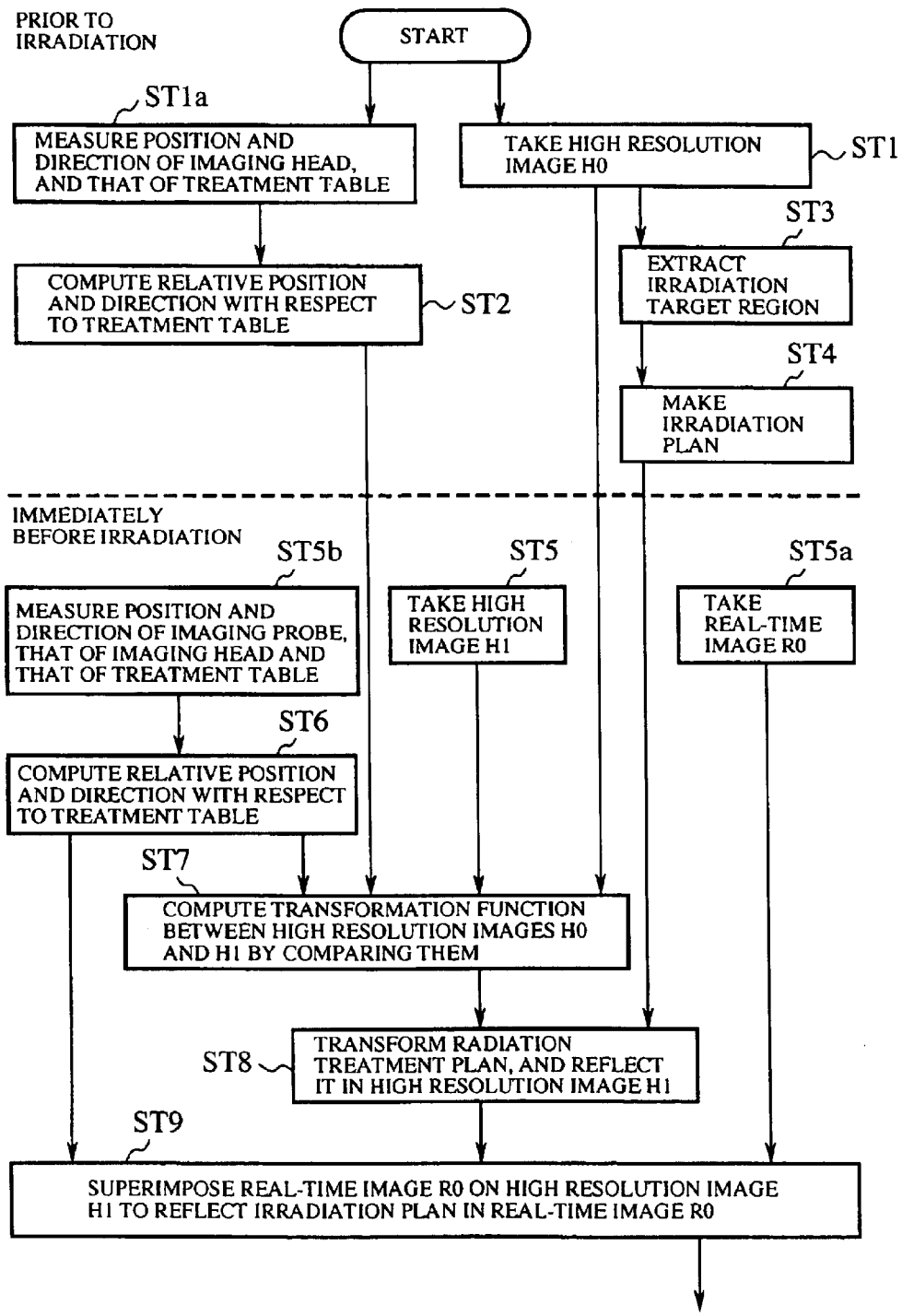
FIG. 3 is a flowchart illustrating the operation of the irradiation system of the embodiment.
Figure 4:
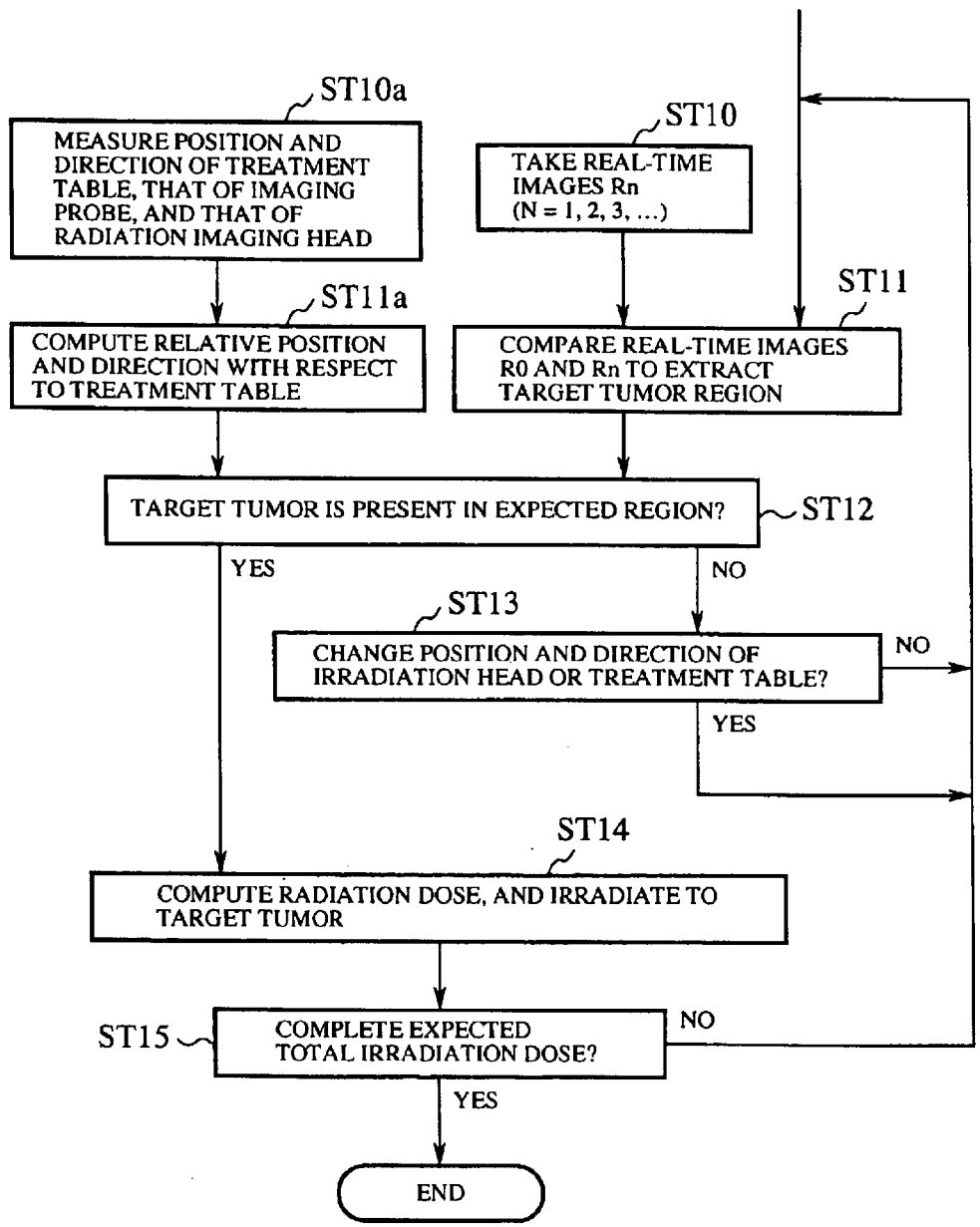
FIG. 4 is a flowchart illustrating the operation subsequent to that of FIG. 3 of the irradiation system of the embodiment.
Figure 5:
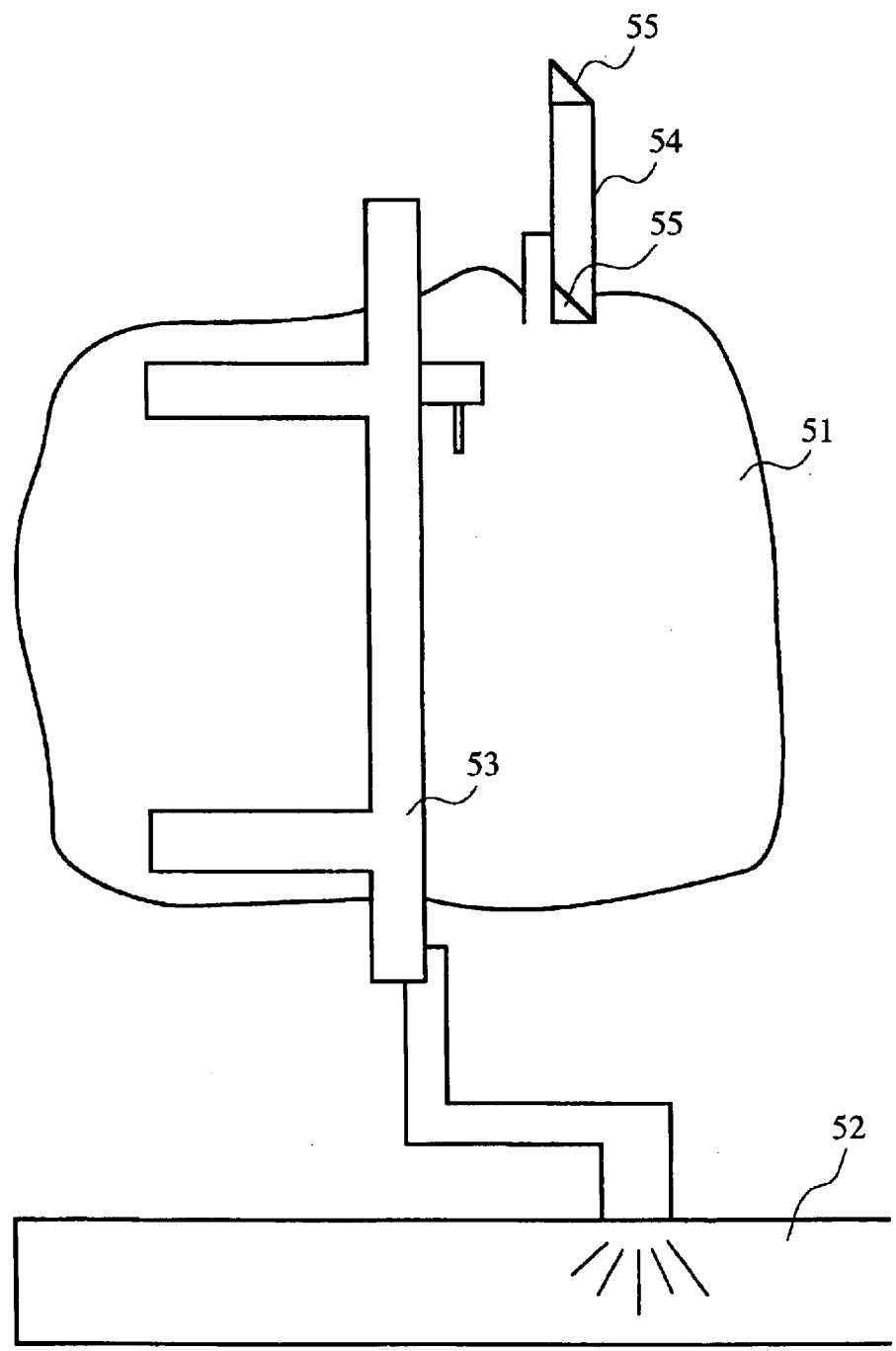
FIG. 5 is a diagram showing an outline of the position recognition of an irradiation target in a conventional irradiation system.

FIGS. 3 and 4 are flowcharts illustrating the operation of the irradiation system of the present embodiment, with reference to which, its operation will be described.

First, prior to actual irradiation, the high resolution imaging device 4 takes a region (irradiation target region) including a tumor, an irradiation target, to plan the radiation treatment. Specifically, when the patient 2 lies down on the treatment table 1, simple markings of the head and feet of the patient 2 are put on the treatment table 1. Then, the surrounding region including a tumor of the lying patient 2 is taken by the high resolution imaging device 4 to capture a set of 3D image data which is referred to as a high resolution image H0 (step ST1, image acquisition step)

In the course of the image acquisition, the 3D position and direction sensor S3 captures the position and gradient of the imaging head of the high resolution imaging device 4 as the detection signal M3, and the 3D position and direction sensor S1 obtains the position and gradient of the treatment table 1 as the detection signal M1 (step ST1a).

These detection signals M1 and M3 are supplied from the 3D position and direction sensors S1 and S3 to the measuring section of position and direction 6 so that it computes the relative position and direction of the imaging head of the high resolution imaging device 4 with respect to the treatment table 1 from the detection signals M1 and M3 (step ST2, position and direction measuring step).

The operation will be described in more detail. Generally speaking, when the position and direction of the imaging head of the high resolution imaging device 4 are specified, the position and direction of the subject for imaging in the image taken by the high resolution imaging device 4 can be determined (that is, the relative position and gradient between the imaging head of the high resolution imaging device 4 and the subject for imaging in the image is usually known).

Thus, using the known relative position and gradient along with the detection signals M1 and M3, the measuring section of position and direction 6 can compute the position and direction of the irradiation target region in the high resolution image H0 in the 3D coordinate system in the work space for measurement having its origin at a point on the treatment table 1.

Subsequently, prior to the actual irradiation, the radiation treatment is planned in accordance with the high resolution image H0 taken by the high resolution imaging device 4.

First, the data processor 7 extracts the irradiation target region from the high resolution image H0 (step ST3, position and direction measuring step). The following methods can be utilized as the extraction method: A first method is based on the luminance of voxels constituting the high resolution image H0 and the gradient of the luminance; and a second method is based on Y. Sato, et al. "Tissue Classification Based on 3D Local Intensity Structure for Volume Rendering", disclosed in IEEE Transactions on Visualization and Computer Graphics, Vol.6, No.2, pp.160–180, 2000, which is based on the distribution of parameters such as the luminance of the voxels constituting the high resolution image H0 and the gradient of the luminance.

As for the irradiation target region extracted as described above, its position and direction in the work space for measurement is computed by the data processor 7.

On the basis of the irradiation target region extracted at step ST3, a physician considers and determines the directions of radiation beams to the region including the irradiation target tumor, the diameter of the radiation beams, irradiation dose, irradiation time and the number of irradiation, thereby planning the radiation treatment (step ST4). Since the radiation treatment is planned on the basis of the high resolution image H0, the content of the plan is reflected in the high resolution image H0.

After the irradiation plan, and prior to the actual irradiation, the patient 2 is laid down on the treatment table 1 with aligning his or her head and feet with the markers written at step ST1. Then, the target tumor and its surrounding region is taken again by the high resolution imaging device 4 (step ST5, image acquisition step). The set of the 3D image data is referred to as high resolution image H1.

In the course of this, the imaging probe of the real-time imaging device 3 is worn on a body surface near the target tumor region of the patient 2, so that the real-time imaging device 3 takes the target tumor and its surrounding region including the tumor (step ST5a, image acquisition step). The set of 3D image data obtained in this case is referred to as real-time image R0. The real-time image R0 is assumed to be taken at time t0.

Furthermore, the 3D position and direction sensor S2 captures the position and gradient of the imaging probe of the real-time imaging device 3 as the detection signal M2, the 3D position and direction sensor S3 captures the position and gradient of the imaging head of the high resolution imaging device 4 as the detection signal M3, and the 3D position and direction sensor S1 captures the position and gradient of the treatment table 1 as the detection signal M1 (step ST5b, position and direction measuring step).

These detection signals M1, M2 and M3 are supplied from the 3D position and direction sensors S1, S2 and S3 to the measuring section of position and direction 6, which computes the relative position and direction of the imaging probe of the real-time imaging device 3 and that of the imaging head of the high resolution imaging device 4 with respect to the treatment table 1 in response to the detection signals M1, M2 and M3 (step ST6, position and direction measuring step).

The operation will be described in more detail. Generally speaking, when the position and direction of the imaging probe of the real-time imaging device 3 is specified, the position and direction of the subject for imaging in the image taken by the real-time imaging device 3 can be determined (that is, the relative position and gradient between the imaging probe of the real-time imaging device 3 and the subject for imaging in the image is usually known).

Thus, using the known relative position and gradient along with the detection signals M1, M2 and M3, the measuring section of position and direction 6 can compute the position and direction of the irradiation target region in the high resolution image H1 in the 3D coordinate system in the work space for measurement having its origin at a point on the treatment table 1.

Subsequently, on the basis of the computation results at steps ST2 and ST6, the high resolution image H0 is superimposed on the high resolution image H1 in the work space for measurement. In this case, the set of image data of the high resolution image H1 does not usually agree with, but has some displacement from that of the high resolution image H0 because of the postural changes of the patient 2 during the two imaging times. Thus, the data processor 7 compares the irradiation target regions of the image data in the two sets of image data.

As the comparing method, the following methods are applicable. First, the irradiation target region extracted from the high resolution image H1 is compared with the irradiation target region extracted from the high resolution image H0 as in the foregoing step ST3; and second, image data are compared such that the mutual information becomes maximum between the sets of image data as disclosed in F. Maes, et al., "Comparative evaluation of multiresolution optimization strategies for multimodality image registration by maximization of mutual information", Medical Image Analysis Vol.3, No.4, pp.373–386, 1999.

As a result of the comparison, the data processor 7 computes the matching between the two sets of image data, and obtains a transformation function incorporating the changes in the irradiation condition from the irradiation plan at step ST4. The foregoing operation corresponds to step ST7. Since the sets of image data are the high resolution images obtained by the high resolution imaging device 4, it is possible to expect highly precise processing result.

Subsequently, according to the transformation function obtained at step ST7, the controller 8 performs the coordinate transformation of the irradiation target region, irradiation expected region and radiation direction in the previous irradiation plan, or makes correction of the radiation dose, thereby reflecting the content of the irradiation plan in the high resolution image H1 (step ST8). More specifically, receiving the transformation function obtained by the data processor 7, the controller 8 supplies the components of the system with the control signals such that the correction according to the transformation function is satisfied. Thus, the irradiation plan is adapted to the actual situation.

Subsequently, according to the relative position and direction of the imaging probe of the real-time imaging device 3 and that of the imaging head of the high resolution imaging device 4 with respect to the treatment table 1 computed at step ST6, the data processor 7 superimposes the high resolution image H1, in which the irradiation plan is reflected, on the real-time image R0 in the work space for measurement (step ST9). Thus, the new irradiation plan is reflected in the real-time image R0.

Here, although the real-time image R0 and the high resolution image H1 are taken in the different modalities, since they are captured at nearly the same time, they can be superimposed in the work space for measurement on the basis of the measurement results of the position and direction by the individual components of the system without considering the sameness of the irradiation target boundaries of the regions extracted from the images. In this case, as for the irradiation target regions captured into the real-time image R0 and the high resolution image H1, the voxels of the irradiation target regions at the same coordinates in the work space for measurement occupy the same position in the irradiation target regions captured into the respective images.

The operation in the step ST8 makes it possible for the information about the irradiation conditions, which are associated with the irradiation target region in the high resolution image H0 and are extracted and decided specifically by the physician, to be reflected on the high resolution image H1, so that the voxels on the real-time image R0 corresponding to the voxels of the irradiation target region in the high resolution image H1 are made the irradiation target region by the operation of the foregoing step ST9. In other words, the content of the irradiation plan is reflected in the real-time image R0 through the high resolution image H0 and the high resolution image H1.

After correcting the irradiation plan as described above, the radiation treatment is started while the patient 2 is lying down on the treatment table 1.

In the course of this, the real-time imaging device 3 continues to take the target tumor and its surrounding region that are captured in the real-time image R0 (step ST10, image acquisition step). Here, the set of image data of the same region taken by the real-time imaging device 3 at time tn, where n=1, 2, 3, . . . , in real-time during the radiation is denoted as real-time image Rn.

At the same time, the 3D position and direction sensor S2 captures the position and gradient of the imaging probe of the real-time imaging device 3 as the detection signal M2, the 3D position and direction sensor S4 captures the position and gradient of the irradiation head of the irradiation device 5 as the detection signal M4, and the 3D position and direction sensor S1 captures the position and gradient of the treatment table 1 as the detection signal M1 (step ST10a, position and direction measuring step).

The detection signals M1, M2 and M4 are supplied from the 3D position and direction sensors S1, S2 and S4 to the measuring section of position and direction 6 so that it computes the relative position and direction of the imaging probe of the real-time imaging device 3 with respect to the treatment table 1 and that of the imaging head of the irradiation device 5 with respect to the treatment table 1 in response to the detection signals M1, M2 and M4 (step ST11a, position and direction measuring step).

The operation will be described in more detail. Generally speaking, when the position and direction of the irradiation head of the irradiation device 5 is specified, the direction of the radiation beam that emanates from the irradiation head and passes through the work space for measurement can be determined (that is, the relative position and gradient between the irradiation head of the irradiation device 5 and the radiation beam is usually known).

Thus, using the known relative position and gradient along with the detection signals M1, M2 and M4, the measuring section of position and direction 6 computes the start position and radiation direction of the radiation beam in the work space for measurement in accordance with the position and direction of the real-time image Rn in the 3D coordinate system in the work space for measurement having its origin at the point on the treatment table 1.

Subsequently, the data processor 7 compares the real-time image R0 with the real-time image Rn. As the comparing image of the two, the methods described above in connection with the foregoing step ST7 can be utilized. According to the result obtained by comparing the real-time image R0 with the real-time image Rn, the data processor 7 identifies the portion in the real-time image Rn, which corresponds to the irradiation target region in the real-time image R0, extracts the target tumor and its surrounding region from the real-time image Rn, and computes the position and direction in the 3D coordinate system in the work space for measurement (step ST11, irradiation target monitoring step).

In this way, the irradiation system of the present embodiment can compute the following items non-invasively without fixing a frame to the patient 2 which is needed in the conventional system: the positions and directions of the components of the irradiation system; the sets of image data; the regions extracted from the sets of image data and assumed to be the irradiation target; and start position and radiation direction of the radiation beam in the work space for measurement. Thus, they can be superimposed on the 3D coordinate system in the work space for measurement, making it possible to monitor the movement of the tumor, the irradiation target, even during the radiation treatment.

Computing the position and direction of the target tumor and its surrounding region from the real-time image Rn in step ST11, the data processor 7 further computes the position and direction of the target tumor against the radiation beam in the 3D coordinate system, and monitors the movement of the target tumor with respect to the radiation beam In this case, the data processor 7 makes a decision as to whether the target tumor is present or not in the region expected in the irradiation plan from the position and direction of the target tumor it computes, thereby deciding whether to administer the radiation or not (step ST12, target position recognizing step).

If the target tumor is not present in the expected region in step ST12, the data processor 7 supplies the controller 8 with correction signals such that the target tumor comes into the expected region, or returns to step ST11 without doing anything, to compare the real-time image R0 with the real-time image Rn, and to extract the irradiation target region, again (step ST13). In response to the correction signals supplied from the data processor 7, the controller 8 supplies the control signals to the components of the system, thereby varying the position and direction of the irradiation head of the irradiation device 5 or that of the treatment table 1.

Thus, at step ST13, the data processor 7 varies the position and direction of the irradiation head or that of the treatment table 1, or waits for the target tumor to come into the expected region.

When the target tumor is present in the expected region at step ST12, the data processor 7 computes the radiation dose from the position and direction of the target tumor with respect to the radiation beam. Receiving the computation result, the controller 8 controls the irradiation device 5 so that it administers the radiation to the target tumor (step ST14).

Computing the total radiation dose from the radiation dose and irradiation time during the irradiation, the data processor 7 sends a signal indicating the end of the radiation to the controller 8 when the total radiation dose reaches a prescribed amount. Receiving the signal, the controller 8 causes the irradiation device 5 to immediately terminate the irradiation. In contrast, when it does not reach the prescribed amount, the data processor 7 continues the irradiation by executing the processing from the step ST10 (step ST15).

Next, consider the arrangement of the components of the irradiation system of the present embodiment.

As for the fixing method of the imaging probe of the real-time imaging device 3 on the body surface, it can be fixed manually by a professional, or by suspending it from an arch disposed over the body surface of the patient 2. In the former case, even if the imaging probe moves a large amount during the image acquisition, the irradiation system of the present embodiment can compute the position and direction of the imaging probe in the work space for measurement from the detection signals M1 and M2 fed from the 3D position and direction sensors S1 and S2 without any problem. Likewise, even if the arch is not fixed to the treatment table 1 in the latter case, the position and direction of the imaging probe can be calculated in the same manner.

As for the arrangement of the treatment table 1, the high resolution imaging device 4 and the irradiation device 5, the following two cases can be implemented: First, all the three components are fixed; and second, the latter two components are fixed with only the treatment table 1 changeable its position by rotation or movement within a range that enables the image acquisition and irradiation.

In the former case, the high resolution imaging device 4 and the irradiation device 5 must be placed such that they do not interfere with each other. However, considering an actual radiation therapy environment, it is more convenient to avoid the interference between the high resolution imaging device 4 and the irradiation device 5 during the treatment by varying the position of the treatment table 1 as in the latter case. In this case, the high resolution imaging device 4 and the irradiation device 5 are disposed in such a manner that they seems to be superimposed in the work space for measurement, although they do not interfere with each other in the actual space.

As described above, the present embodiment is configured such that it captures sets of image data of the irradiation target region non-invasively without fixing a frame to the patient 2, superimposes and compares the images in the work space for measurement to recognize the position and direction of the irradiation target by monitoring the movement thereof. As a result, the present embodiment can reduce the radiation exposure to unnecessary regions, and irradiate only the desired target intensively and concentratedly.

In addition, the present embodiment is configured such that it measures the position and direction between the treatment table 1, real-time imaging device 3, high resolution imaging device 4, and irradiation device 5 in the 3D coordinate system in the work space for measurement. Thus, the present embodiment can detect precise positions and directions of the components of the system in the 3D coordinate system in the work space for measurement, thereby making it possible to administer precise radiation to the irradiation target.

Moreover, the present embodiment is configured such that the data processor 7 compares the irradiation target regions in the images taken by the imaging device of the same modality, and obtains the position and direction of the irradiation target region in the images. As a result, it is unnecessary for the present embodiment to consider the sameness of the boundary conditions, which is required for comparing the irradiation target regions in the images taken by the imaging devices of the different modalities. Thus, the present embodiment can make precise comparison between the irradiation target regions in the images.

Although the foregoing embodiment handles an example that applies the irradiation system in accordance with the present invention to the radiation therapy, the present invention is not limited to this field. In addition, although the irradiation target movement monitoring method and irradiation target position recognizing method in accordance with the present invention derive their concept from the operation to the irradiation target, they do not necessarily relate to a treatment method.

What is claimed is:

1. A radiation system comprising:
    irradiation target positioning means for positioning an object having an irradiation target to be subjected to irradiation;
    fixed, unmovable in a lateral direction, irradiation target imaging means for non-invasively taking images of an irradiation target region including the irradiation target;
    irradiation means for administering radiation to the irradiation target region according to prescribed irradiation conditions;
    position and direction measuring means for measuring positions and directions of said irradiation target positioning means, said irradiation target imaging means and said irradiation means, and for computing relative positions and directions between them;
    irradiation condition correcting means for obtaining position and direction of the irradiation target region in the images using computation results of said position and direction measuring means and compared results obtained by comparing the irradiation target regions in the images successively taken, including at least a first image and a second image taken after said first image and shortly before irradiation of the target, by said irradiation target imaging means, and for correcting the irradiation conditions in which the obtained position and direction is reflected by modifying an irradiation plan initially generated from said first image;
    control means for controlling the radiation to the irradiation target region in response to the irradiation conditions obtained as a result of the correction by said irradiation condition correcting means in accordance with the modified irradiation plan; and
    wherein said position and direction measuring means measures positions and directions of said irradiation target positioning means, said irradiation target imaging means, and said irradiation means in a 3D coordinate system.

2. The radiation system according to claim 1, wherein said irradiation target imaging means comprises a plurality of imaging devices of different modality, and wherein
    said irradiation condition correcting means obtains the position and direction of the irradiation target region in the images using computation results obtained by said position and direction measuring means and compared results obtained by comparing the irradiation target region in the images taken by said imaging device of the same modality among the images successively taken by said plurality of imaging devices of different modality.

3. The radiation system according to claim 1, wherein said irradiation target imaging means comprises: a high resolution imaging device for taking high resolution 3D images of the irradiation target region which are used for setting the irradiation condition; and a real-time imaging device for taking high resolution 3D images of the irradiation target region before and during irradiation, and wherein said irradiation condition correcting means obtains the positions and directions of the irradiation target regions in the images using the computation results obtained by said position and direction measuring means, compared results obtained by comparing the irradiation target regions in the images taken by said high resolution imaging device, and compared results obtained by comparing the irradiation target regions in the images taken by said real-time imaging device, and corrects the irradiation conditions using the images which are acquired by said high resolution imaging device and by said real-time imaging device, and in which the obtained positions and directions are reflected.

4. An irradiation target movement monitoring method of an irradiation system including irradiation target positioning means for positioning an object having an irradiation target to be subjected to irradiation, fixed, unmovable in a lateral direction, irradiation target imaging means for taking images of an irradiation target region including the irradiation target, and irradiation means for administering radiation to the irradiation target region according to prescribed irradiation conditions in accordance with a modified irradiation plan, said irradiation target movement monitoring method comprising:

an image acquisition step of successively and non-invasively taking images of the irradiation target region by said fixed irradiation target imaging means;

a position and direction measuring step of measuring positions and directions of said irradiation target positioning means, said irradiation target imaging means, and said irradiation means in a 3D coordinate system, and of computing relative positions and directions between them; and an irradiation target monitoring step of obtaining positions and directions of the irradiation target regions in the images using computation results obtained by said position and direction measuring means and compared results obtained by comparing the irradiation target regions in the images successively taken, including at least a first image and a second image taken after said first image and shortly before irradiation of the target, in the image acquisition step and of correcting the irradiation conditions by reflecting the positions and directions is the images by modifying an irradiation plan initially generated from said first image.

5. The irradiation target movement monitoring method of an irradiation system according to claim 4, wherein the irradiation target monitoring step obtains the positions and directions of the irradiation target regions in the images using computation results obtained in the position and direction measuring step and compared results obtained by comparing the irradiation target regions in the images successively taken by said irradiation target imaging means of the same modality.

6. A irradiation target position recognizing method of an irradiation system including irradiation target positioning means for positioning an object having an irradiation target to be subjected to irradiation, fixed, unmovable in a lateral direction, irradiation target imaging means for taking images of an irradiation target region including the irradiation target, and irradiation means for administering radiation to the irradiation target region according to prescribed irradiation conditions in accordance with a modified irradiation plan, said irradiation target position recognizing method comprising:

an image acquisition step of successively and non-invasively taking images of the irradiation target region by said fixed irradiation target imaging means;

a position and direction measuring step of measuring positions and directions of said irradiation target positioning means, said irradiation target imaging means, and said irradiation means in a 3D coordinate system, and of computing relative positions and directions between them; and a target position recognizing step of obtaining positions and directions of the irradiation target regions in the images using computation results obtained by said position and direction measuring means and compared results obtained by comparing the irradiation target regions in the images successively taken, including at least a first image and a second image taken after said first image and shortly before irradiation of the target, in the image acquisition step, and of correcting the irradiation conditions by reflecting the positions and directions in the images by modifying an irradiation plan initially generated from said first image.

7. The irradiation target position recognizing method of an irradiation system according to claim 6, wherein the target position recognizing step obtains the positions and directions of the irradiation target regions in the images using computation results obtained in the position and direction measuring step and compared results obtained by comparing the irradiation target regions in the images successively taken by said irradiation target imaging means of same modality.

8. A radiation system, comprising:

a positioning device for positioning an object including an irradiation target;

an irradiation device;

at least one fixed, unmovable in a lateral direction, imaging device for non-invasively generating images of an irradiation target region including said irradiation target;

a measuring device for measuring position and direction of said irradiation target based on said generated images using a three-dimensional coordinate system including coordinate positions of said positioning device, said irradiation device, and said at least one measuring device;

a processing device for determining a current position and direction of said irradiation target based on comparing successive generated images, including at least a first image and a second image taken after said first image and shortly before irradiation of the target, input from said measuring device using a predetermined algorithm; and a controller for directing said irradiation device to irradiate said irradiation target based on said current position and direction of the irradiation target by modifying an irradiation plan initially generated from said first image.

9. The radiation system of claim 8, wherein said at least one imaging device to generate said images in at least two different forms.

10. A method of radiating, comprising:

positioning an object including an irradiation target;

generating images non-invasively of an irradiation target region including said irradiation target using a fixed, unmovable in a lateral direction, imaging device;

measuring position and direction of said irradiation target based on said generated images using a three-dimensional coordinate system including coordinate positions of said positioning device, said irradiation device, and said at least one measuring device; and determining a current position and direction of said irradiation target based on comparing successive generated images, including at least a first image and a second image taken after said first image and shortly before irradiation of the target, input from said measuring device using a predetermined algorithm; and irradiating said irradiation target based on said current position and direction of the irradiation target by modifying an irradiation plan initially generated from said first image.

11. The method of claim 10, wherein said generating includes generating said images in at least two different forms.

* * * * *